United States Patent [19]

Eibofner

[11] Patent Number: 5,674,068
[45] Date of Patent: Oct. 7, 1997

[54] MEDICAL OR DENTAL HANDPIECE

[75] Inventor: Eugen Eibofner, Biberach, Germany

[73] Assignee: Kaltenbach & Voigt GmbH & Co., Biberach, Germany

[21] Appl. No.: 443,336

[22] Filed: May 17, 1995

[30] Foreign Application Priority Data

May 20, 1994 [DE] Germany .............. 44 17 810.7

[51] Int. Cl.⁶ .............................................. A61C 1/10
[52] U.S. Cl. ...................................... 433/114; 433/126
[58] Field of Search .......................... 433/114, 141, 433/126, 133

[56] References Cited

U.S. PATENT DOCUMENTS

| | | | |
|---|---|---|---|
| 2,249,058 | 7/1941 | Staunt | 433/114 |
| 2,568,708 | 9/1951 | Bjorklund | 279/51 |
| 3,050,856 | 8/1962 | Staunt | 433/126 |
| 3,955,284 | 5/1976 | Balson | 32/27 |
| 4,642,051 | 2/1987 | Löhn | 433/126 |
| 4,941,828 | 7/1990 | Kimura | 433/114 |

FOREIGN PATENT DOCUMENTS

| | | | |
|---|---|---|---|
| 0017861 | 10/1980 | European Pat. Off. | 433/114 |
| 0054653 | 6/1982 | European Pat. Off. | |
| 0159453A1 | 10/1985 | European Pat. Off. | |
| 2174399 | 10/1993 | France | |
| 90689 | 3/1897 | Germany | |
| GM7910126 | 9/1980 | Germany | |
| 3142534 | 10/1981 | Germany | 433/114 |
| 3142534 | 8/1986 | Germany | |

*Primary Examiner*—Cary E. O'Connor
*Attorney, Agent, or Firm*—Fitzpatrick, Cella, Harper & Scinto

[57] ABSTRACT

A medical or dental handpiece having a grip sleeve formed with an outer gripping surface structure which provides improved grippability. The outer gripping surface structure is formed with alternate grooves and corrugations extending circumferentially around the sleeve and which, in cross-section, are axially spaced from each other. The grooves and corrugations are rounded concavely and convexly, respectively.

12 Claims, 3 Drawing Sheets

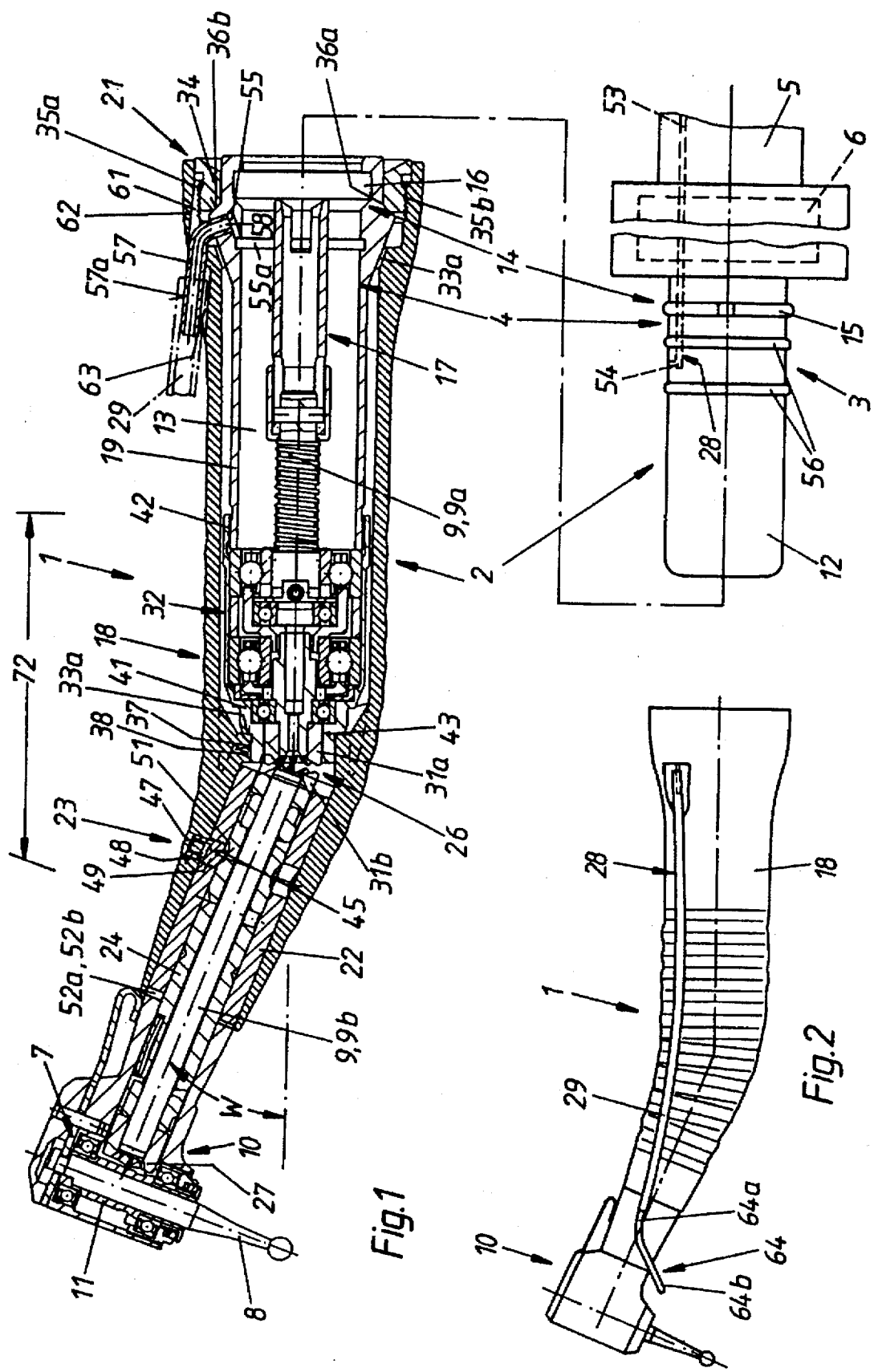

MEDICAL OR DENTAL HANDPIECE

BACKGROUND OF THE INVENTION

1. Field of the Invention

The invention relates to a medical or dental handpiece having a grip sleeve which extends with a straight or angled shape and has at its forward end a tool holder having a mounting device for a treatment tool arranged transversely of or along the longitudinal axis of the handpiece, and at its rearward end is releasibly connectable with a supply part by means of a coupling device, the grip sleeve having in the grip region which is grasped by an operating hand a superficial surface structure on its external surface which improves the grippability.

2. Description of the Related Art

Several demands are made of a handpiece of the kind being considered. On the one hand, it should be of a configuration which is easy to handle, so that the person carrying out a treatment can grasp it easily without exercising great force and attention and can hold and control the handpiece during treatment. This demand is of great significance because the quality of the treatment is dependent thereupon, the standard of which—in the treatment of the human or animal body—can have lasting positive or negative consequences. Thereby, the handpiece should be light, so that the person carrying out the treatment is able to guide it without great effort in terms of force. For the same reason, it should be securely grippable, to which end several superficial surface structures have already been proposed, e.g. projections arranged in circular ring form (DE 31 41 534 C2) trough-like flattenings adjacent one another (DE-GM 79 10 126) and grains or granulations embedded in the surface of the handpiece (EP-0 054 653 A2).

Practice has shown that the superficial surface structure should on the one hand be securely grippable but, on the other hand, should exert a non-taxing effect on the hand of the person carrying out a treatment so that even after an extended treatment time the skin of the hand effecting the treatment is not subjected to excessive demands or irritated, which could influence or impair the treatment and also the quality of the treatment.

On the other hand, a handpiece of the kind being considered is a product the manufacturing costs of which should be small, so that the treatment costs can also be kept down.

SUMMARY OF THE INVENTION

The object of the invention is to so configure a medical or dental handpiece of the kind under consideration that handling is easier to carry out, whilst reliable guidance is ensured.

According to one aspect of this invention, there is provided a superficial surface structure for the handpiece in its grip region which—avoiding edges—is of soft structure and thus exerts a non-taxing and pleasant effect on the hand of the person carrying out a treatment, good graspability being attained which ensures the sought after reliable and light handling during the treatment.

According to a further aspect of the invention not only can the weight of the handpiece be reduced but also its manufacturing costs, because the grip sleeve as a molded part, in particular of plastics, can be manufactured more economically and quickly and thus more cost effectively. Furthermore, this configuration leads to an improved heat insulation of the grip sleeve, whereby handling is likewise facilitated.

According to further features of the invention, which is described herein the handling of the handpiece is improved simple and cost effective manufacturable constructions of compact dimensions are allowed mounting and de-mounting are simplified and possibilities are opened up for providing a handpiece with different features, in particular tool speeds of rotation, by variations of the assembly.

BRIEF DESCRIPTION OF THE DRAWINGS

Below, the invention and further advantages which can be achieved thereby will be described in more detail with reference to preferred exemplary embodiments and the drawings. In the drawings:

FIG. 1 is a side view, taken in axial section, of a medical or dental treatment instrument having a handpiece in accordance with the invention;

FIG. 2 is a side view of the handpiece of FIG. 1;

DETAILED DESCRIPTION OF THE PREFERRED EMBODIMENTS

Figure 3:
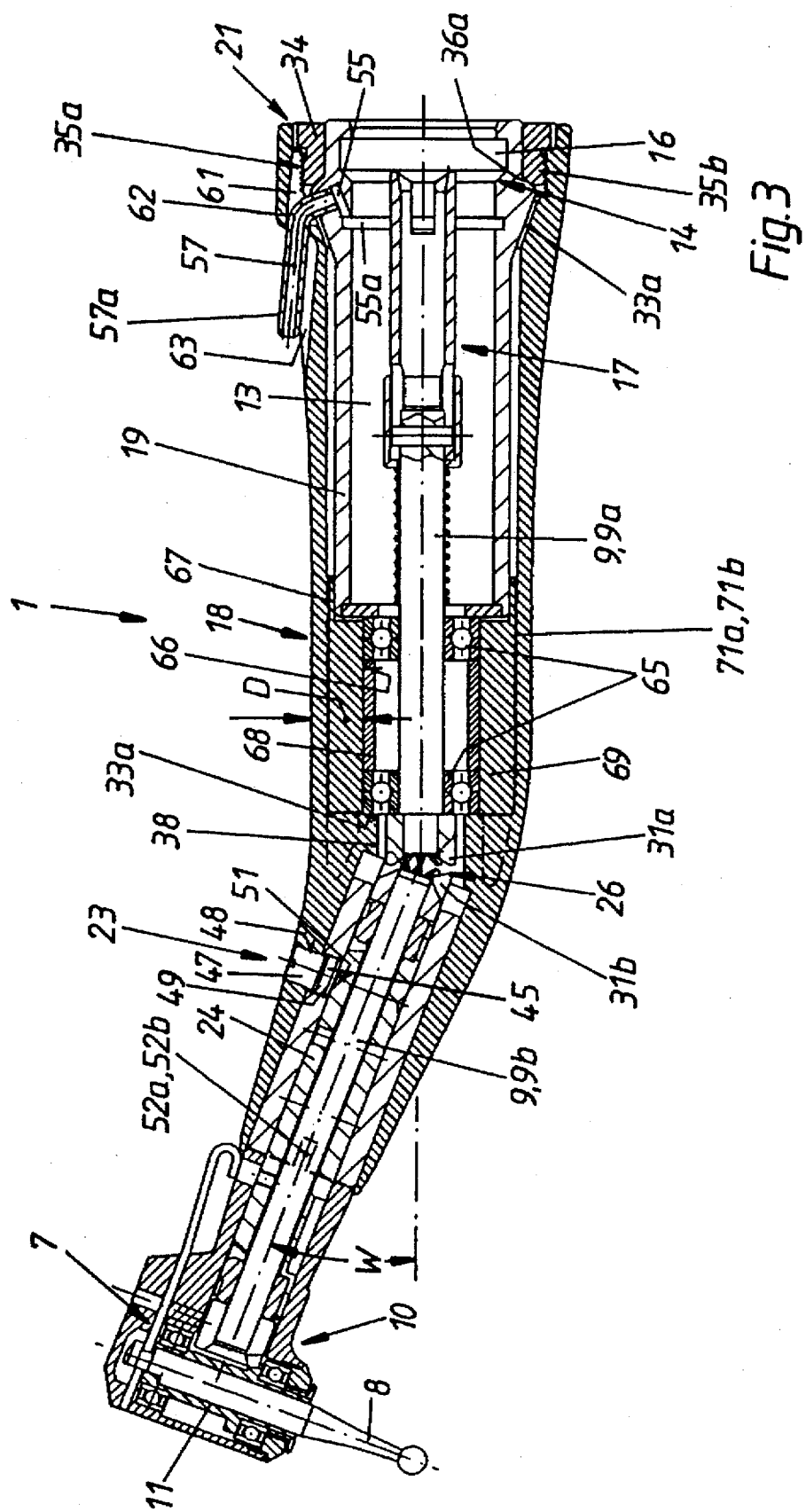
FIG. 3 is a view similar to FIG. 1 and showing a handpiece in accordance with the invention in axial section, in a modified configuration.

In the present exemplary embodiment shown in FIG. 1, a handpiece 1 is an exchangeable part of a dental treatment instrument 2 which comprehends the handpiece 1 and a supply part 3 to which the handpiece 1—at its rear end—can be readily and quickly coupled by means of a plug-in/rotary coupling 4 and which can be connected to a supply system by means of a supply line 5 to the rear, which supply system delivers the drive energy and treatment media for the treatment instrument 2, which are supplied through supply lines running in the flexible supply line 5.

A drive motor 6 for a treatment tool 8, in this case a drill, which can be mounted at the forward head end of the handpiece 1 in a mounting device 7, is arranged as an electric motor in the supply part 3 and is drivingly connected with a mounting sleeve 11 which receives the tool by means of a drive train 9 which extends axially in the handpiece 1 and is rotatably mounted therein. The tool 8 is mounted to be rotatable transversely of the longitudinal middle axis of the handpiece 1, in a handpiece head 10 having the mounting sleeve 11, and the tool thus faces towards the so-called tool side.

The plug-in/rotary coupling 4 is formed by means of a cylindrical coupling pin 12 and a hollow cylindrical coupling recess 13 into the which the coupling pin 12 can be inserted and, in the inserted position, releasibly latched, whereby in the latched position the rotatability of the handpiece 1 on the coupling pin 12 is ensured. The latching device 14, which can be overcome by the application of force, is formed by a latch element 15—mounted in a recess of the coupling pin 12 or of the coupling recess 13 and biased by a spring or formed by a spring—for example a spring ring which is capable of latching into a corresponding ring-shaped latch groove 16 in a manner which can be overcome by the application of force.

In the present configuration the coupling pin 12 is arranged on the supply part 3, from which it axially projects, whilst the coupling recess 13 is arranged in the handpiece 1 and is open rearwardly. The drive train 9 has at its rearward end a plug-in coupling part 17 that, upon axial plugging together of the handpiece 1 and the supply part 3, is self-actingly couplable with a corresponding complementary plug-in coupling part (not shown) on the supply part 3. The coupling pin 12 is formed by means of a forwardly open sleeve into which, upon plugging together, the rearward end region of the drive train 9 is introduced so that the coupling pin 12 engages over the portion of the drive train 9 extending into the coupling recess 13.

The main parts of the handpiece 1, formed in the shape of a so-called angled piece, are a grip sleeve 18 the forward end region of which is angled at an acute angle W of approximately 21° to the side away from the tool 8, a rear reinforcing sleeve 19—in particular of metal—which can be placed into the grip sleeve 18 from the rear and can be fixed therein by means of a fixing device 21, a forward reinforcing sleeve 22—in particular of metal—which can be placed from the front into a cylindrical hole of the grip sleeve 18 and can be fixed therein by means of a fixing device 23, the handpiece head 10, which receives the tool 8 and is rotatably mounted, and which can be placed from the front into the forward reinforcing sleeve 22 with a rearward cylindrical plug-in coupling pin 24 and is secured therein by means of the fixing device 23 against unintended pulling out to the front and against rotation, the drive train 9 which comprises a rear drive train part 9a which extends to the angle point 26 of the grip sleeve 18 and a forward drive train part 9b, which extends from the angle point 26, in the plug-in coupling pin 24, into the handpiece head 10 in which it is drivingly connected with the mounting sleeve 11 for the tool 8 by means of an angled gear transmission 27, and a media line 28 for a treatment medium, preferably water, which extends outside of the grip sleeve 18 at the outer surface thereof in the form of a small flexible hose 29 from the rearward end of the handpiece 1 to the handpiece head 10 in the region of which it is directed towards the treatment site. The drive train parts 9a, 9b are drivingly connected with one another in the region of the angle point 26 by means of two bevelled gears 31a, 31b mounted thereon. In the rear drive train 9a there may be integrated a step-up or step-down transmission 32 which in the exemplary embodiment according to FIG. 1 is connected as a constructional unit with the rear reinforcing sleeve 19 and can thus be installed or removed with this sleeve. The forward drive train part 9b is received and mounted in an axial mounting bore of the plug-in coupling pin.

For mounting the rear reinforcing sleeve 19, the grip sleeve 18 has a centering means and a shoulder surface 33a against which the rear reinforcing sleeve 19 can be biassed with a corresponding shoulder surface 33b on the transmission 32. For this purpose there is provided a ring nut 34 which, with an external thread 35a, can be screwed into an internal thread 35b arranged at the rear end of the grip sleeve 18 and which presses against a rearwardly facing shoulder surface 36b on the reinforcing sleeve 19 with a shoulder surface 36a. In the present configuration, the shoulder surface pair 36a, 36b are forwardly diverging conical surfaces which form a centering means for the reinforcing sleeve 19 in the rear region of the grip sleeve 18. A second centering means for the forward region of the rear reinforcing sleeve 19 is provided in the middle region of the grip sleeve 18—in the configuration in accordance with FIG. 1 directly behind the angle point 26—and the centering means is formed by means of a coaxial cylindrical hole 37 in the region of an inner angular projection 38 with the rearwardly facing approximately radial shoulder surface 33a. In the configuration according to FIG. 1, the transmission 32 is arranged in an internal housing 41 as a unit which is screwed together with, preferably screwed onto, the forward end of the rear reinforcing sleeve 19 by means of a rear thread 42.

The internal housing 41 has at its forward end a cylindrical projection 43 which sits in the hole 37, with tolerance, and is thus centered.

The fixing device 23 for the handpiece head 10 is formed by means of an arresting screw 45 having an in particular conical arresting portion which is screwed, from the outside, into a cylindrical hole 48 which receives its screw head 47, with tolerance, and into a threaded hole 49 of the forward reinforcing sleeve 22 and which can be Screwed—with its in particular conical arresting portion —into a correspondingly formed indentation in the plug-in coupling pin 24. By means of the arrangement of a plurality of indentations 51, arranged distributed around the circumference, it is possible to retain the handpiece head 10 selectively in a plurality of rotational positions which are rotated with respect to the illustrated position. In order more easily to be able to find these positions there is provided between the handpiece head 10 and the grip sleeve 18 or the forward reinforcing sleeve 22 a latch engagement means having a recess and a latch projection 52a which fits therein and in the present configuration is arranged rearwardly on the handpiece head 10, there being provided in each respective desired rotational position respective opposing latch recesses 52b. A preferred rotational position, having a corresponding indentation 51 and latch recess 52b, is provided which is rotated by 180° with respect to the illustration in FIG. 1.

The media line 28 penetrates through the plug-in/rotary coupling 4 radially in such a manner that through-flow is ensured in any rotational position. For this purpose, an initially axis-parallel and then radially extending media channel 53, 54 opens at the outer surface of the coupling pin 12, a radial media channel 55 leading further in the rear reinforcing sleeve 19 in the same radial plane. The sealing of the gap between the coupling pin 12 and the coupling recess 13 is effected by means of sealing rings 56 arranged to the two sides of the exit or entrance openings, which rings can each sit in an external groove of the coupling pin 12 or in an internal groove of the coupling recess 13. In order to ensure through-flow in any rotational position there is arranged an annular groove 55a in the transverse plane of the channel opening in the external surface of the coupling pin 12 or in the internal surface of the coupling recess 13. The media channel section 55 extends to an outwardly opening round hole 58 in the reinforcing sleeve 19 in which an angled connection pipelet 57 is fixedly and sealingly emplaced, for example soldered in or glued in. The bent-away pipe section 57a is arranged approximately axis-parallel or slightly outwardly diverging and it projects through and projects over the grip sleeve 18 to the outside and to the front, in a through hole 61, The hose 29 is pushed onto the external pipe section 57a. The pipe section 57a penetrates the grip sleeve 18 in the region of a radially extending wall 62 which may be formed by means of a step-like cross-sectional enlargement of the grip sleeve 18 or by means of an external recess 63 in the grip sleeve 18. The recess 63 is of a size such that the hose 29 can be pushed on.

This configuration is of particular advantage because it requires no sealing between the connection pipelet 57 and the grip sleeve 18. Further, it requires no attachment of the connection pipelet 57 to the grip sleeve. The connection pipelet 57 is, upon assembling the rear reinforcing sleeve 19 into place, automatically brought into its mounting position externally on the grip sleeve without need for subsequent sealing. This is made possible by means of the approximately axis-parallel extension of the pipe section 57a and of the hole 61.

The forward end of the hose 29 is pushed on to a second connection pipelet 64 (FIG. 2) which is attached, for example soldered or glued, in a side position on the handpiece head 10 and is so angled that its rear pipe section 64a is approximately axis-parallel directed and its forward pipe section 64b is directed towards the treatment site. For reasons of handling; the rear connection pipelet 57 is located in the middle position of the upper right or left (for a right-handed person) quadrant, when viewed from the rear (FIG. 2).

The exemplary embodiment according to FIG. 3, in which the same or similar parts are provided with the same reference signs, differs from the above-described exemplary embodiment solely in a different formation and configuration of the mounting of the forward end of the rear drive train part 9a. In those cases in which a different—or even no—transmission 32 is to be provided, as shown in FIG. 3, there is employed a transmission unit with an internal housing 41 of different size or no transmission is employed, merely mounting parts, according to FIG. 3 one or two roller bearings 65 with different cross-sectional dimensions. For such cases it is possible to provide a plurality of grip sleeves 18 which differ with regard to the wall thickness indicated by D in FIG. 3 and which have each a cylindrical mounting hole 66 matched to the diameter of the roller bearings 65. Since with such a configuration there is no separate internal housing 41 as of the first exemplary embodiment there is needed a centering means of the forward end of the rear reinforcing sleeve 19. This centering means may be formed by means of a cylindrical ring portion 67 in the grip sleeve 18, in which ring portion the forward end region of the reinforcing sleeve 19 sits with tolerance, possibly being screwed in (thread 42). For axial positioning of the reinforcing sleeve 19 there likewise serves the shoulder surface 33a, the reinforcing sleeve 19 being biassed or restricted against the shoulder surface 33a by means of one or two of the roller bearings 65 and a spacing sleeve 68.

Preferably, however, only one and the same grip sleeve 18 is employed for above-described different configurations, a radial spacing sleeve 69 being emplaced in the grip sleeve 18 for matching of the corresponding cross-sectional dimension or for mounting the roller bearings 65, the external cross-sectional dimension 71a of the radial spacing sleeve being matched with tolerance to the internal cross-sectional dimension 71b of the grip sleeve 18 and bearing against the shoulder surface 33a and being axially securable by means of suitable means. For this purpose, the spacing sleeve 69 may be, for example, pressed in or glued in or, for exchangeable attachment, there may be arranged a corresponding internal thread on the internal surface of the grip sleeve 18 and a corresponding external thread on the external surface of the spacing sleeve 69, so that the letter can be screwed in. In this case it is advantageous to arrange engagement elements, for example recesses or projections, at the rear end of the spacing sleeve 69 which elements allow screwing-in or screwing-out by means of a suitable tool. It is thereby advantageous to arrange the ring portion 67 as a piece rearwardly on the spacing sleeve 69. For transmissions 32 or mounting elements (roller bearings) of differing sizes there may be provided a plurality of spacing sleeves 69 in each case having an internal cross-section adapted to the size.

For a handpiece 1 the superficial surface form and structure in the grip region 72 of the grip sleeve 18 is of substantial importance, since the grippability is dependent therefrom. There is a requirement for such a superficial surface structure that the handpiece lays or can be held stably and securely on the hand of the user without the grasping surface of the operating hand or the fingers thereof being the subject of excessive demands. Thereby, it is to be taken into consideration that in operation of the handpiece slight vibrations can hardly be avoided which increase the pressure demands of the grip surfaces.

With the present configuration preferably two measures serve for meeting these requirements, namely on the one hand a corrugated or rippled outer surface and on the other hand a slight roughness of the outer surface in the grip region 72. Thereby, the form of the grip sleeve 18 also has a significant influence in providing a comfortable and secure grasping and holding of the handpiece 1.

Figure 4:
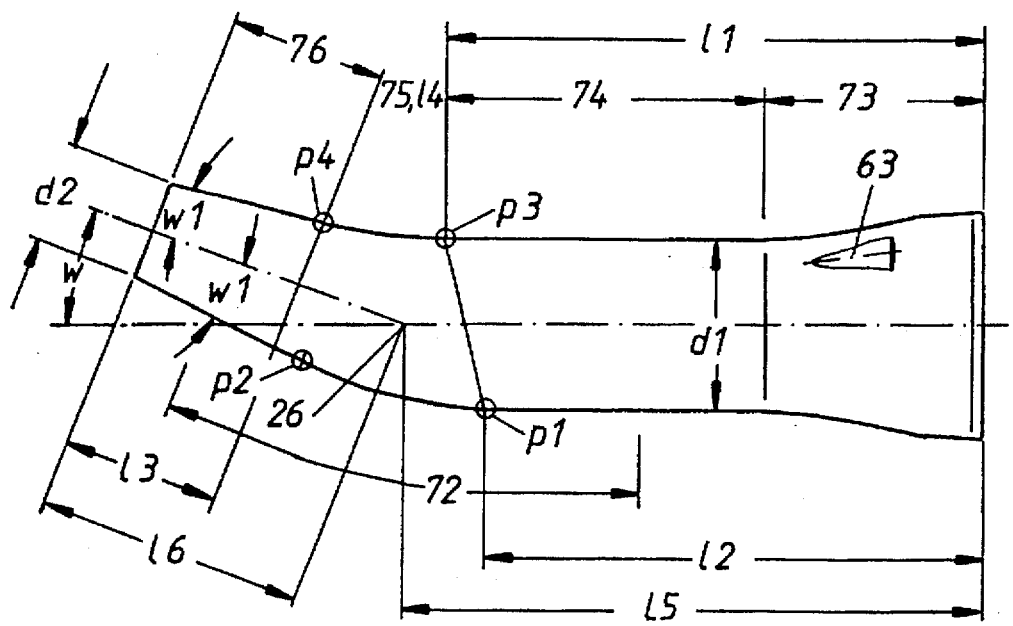
FIG. 4 is a representation of the basic shape of a grip sleeve shown in side view.
Figure 5:
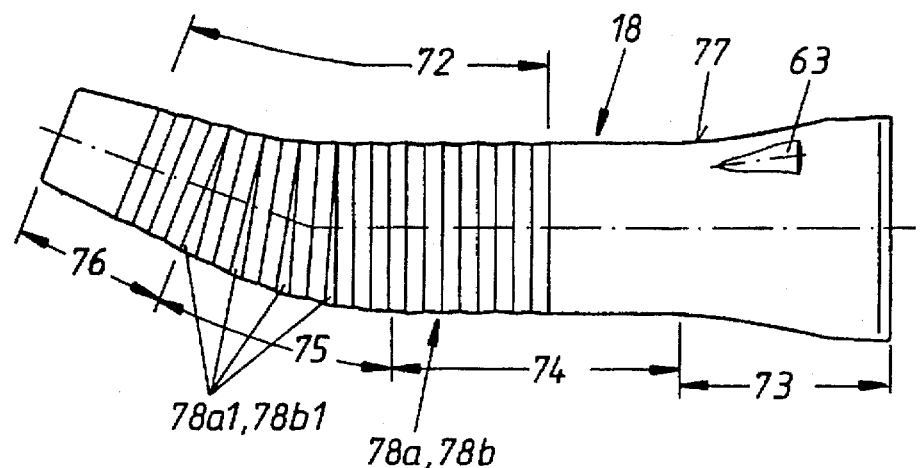
FIG. 5 is an external side view of the grip sleeve of FIG. 4.

Below, the basic form of the grip sleeve 18 in the grip region 72 will be described with reference to FIG. 4. The grip sleeve can be divided from the rear to the front, in sequence, into four shape sections 73, 74, 75, 76. The first shape section 73 is, relative to the second cylindrical shape section 74, rearwardly divergingly thickened, whereby this thickening may be conical or initially slightly concave rearwardly and then slightly convexly rounded, as is shown in the Figures. The third shape section 75 is in the region of the angle point 26. In the region of this shape section 75 the grip sleeve 18 is curved and at the same time forwardly tapered in cross-section, whereby the ratio of the cross-sectional dimensions at the beginning and at the end of this shape section 75 is approximately 1.2 to 1. The fourth shape section 76 is concentrically conically tapered towards the forward end, whereby the taper ratio in the region of the third shape section 75 and of the fourth shape section 76 is approximately equal. Preferably, the beginning points p1 and p2 of the third and fourth shape sections 75, 76 on the convex side of the grip sleeve 18 are somewhat rearwardly displaced relative to the beginning points p3 and p4. The outer diameter d1 of the grip sleeve 18 in the region of the second shape section 74 is about 13 to 17 mm, in particular approximately 15.2 mm. From this cross-sectional dimension, the grip sleeve 18 tapers to an external diameter d2 of about 7 to 11 mm, in particular approximately 9 mm, at its forward end. The length of the first and second shape sections 73, 74 on the concave side of the grip sleeve 18, see $l_1$, is about 35 to 65 mm, preferably approximately 47.4 mm, and on the convex side, see $l_2$, about 20 to 45 mm, preferably approximately 41.3 mm. The central length $l_3$ of the fourth shape section 76 is about 12 to 20 mm, in particular approximately 15 mm. The beginning and end points p3, p4 of the third shape section 75 on the concave side of the grip sleeve 18 have a spacing $l_4$ from one another which is somewhat less than the length $l_3$, namely about 7 to 13 mm, in particular approximately 10 mm. The spacings $l_5$, $l_6$ of the angle point 26 in the middle region of the third shape section 75 from the rear and forward ends are respectively about 40 to 70 mm, in particular approximately 50.5 mm, and about 20 to 30 mm, in particular approximately 23.2 mm.

The convergent outer surface in the fourth shape section 76 encloses an angle w1 of about 3° to 9°, in particular approximately 6.2°, with the associated longitudinal middle axis.

Figure 6:
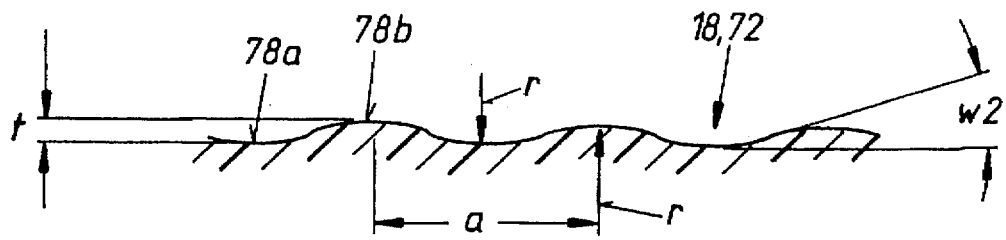
FIG. 6 is a fragmentary section view showing a surface shape of the grip sleeve in axial section and in an enlarged representation.

In the grip region 72 which begins in the middle region of the second shape section 74 and extends to the middle region of the fourth shape section 76, the external surface 77 of the grip sleeve 18 is slightly corrugated by means of circumferentially running, preferably continuous, grooves 78a and corrugations 78b which, as shown in FIG. 6, are rounded concavely and convexly, respectively in cross-section and may have a sine wave shape. Preferably, the radius r of the grooves 78a is equal to the radius r of the corrugations 78b and is about 3 to 5 mm, in particular approximately 4 mm. The axial spacing a between two neighbouring grooves or corrugations is about 2 to 4 mm, preferably approximately 3.1 mm. The middle angle w2 of the flanks is about 10° to 30°, in particular approximately 21°. It has been determined from trials that a groove depth t of about 0.015 to 0.3 mm, in particular approximately 0.15 mm, is very suitable.

The corrugations and grooves preferably run parallel to one another. To compensate for the curvature there may be provided a plurality, for example, four compensation grooves or corrugations 78a1, 78b1 which widen towards the convex side with a wedge shape.

Further, at least the flanks of the corrugations 78b and preferably also the corrugation peaks, and most preferably the external surface 77 in the grip region 72 as a whole, including also the grooves 78a, have a slight roughness which in particular together with the corrugated form make possible a holding in the operating hand which is not taxing for the skin of the operating hand and still allows secure grasping in the operating hand. Preferably, the external surface 77 is correspondingly rough over the whole length region of the grip sleeve 18, whereby the grippability is improved also in the case of other manipulations of the handpiece 1 such as for example upon grasping and plugging onto the supply part 3. Trials have shown that a depth of roughening of the class K of about 1.5 to 4 μm, in particular approximately 2.24 μm is advantageously suitable (see VDI 3400(VDI guide lines).

The grip sleeve 18 may be of corrosion resistant metal, in particular stainless steel, ceramics or preferably plastics, in particular fiber-reinforced plastics. It has likewise been determined in the trials, that polyetheretherketone (PEEK), in particular reinforced with glass fibers or carbon fibres, is particularly well suited. By these means the requirements to be met are fulfilled, namely great strength (in particular resistance to bending strain and tensile strength), temperature resistance, resistance to chemicals and resistance to radiation, with low weight. A PEEK thermoplastics which is well suited is available under the designation Victrex.

With those materials which can be produced by molding, for example metal, plastics and ceramics, a simple and economical provision of the roughness is afforded when this is formed in the production by means of a corresponding roughness of the relevant mold surfaces of the mold. This method of production is particularly suitable for fiber-reinforced materials, in particular plastics, since by means of this method the fibres remain embedded in the material.

Within the scope of the invention it is, however, also possible and advantageous, in particular with metallic materials, to produced the roughness or erosion structure by means of erosive working of the external surface 77. This may be electro-erosion processing, spark erosion, arc erosion or an erosion by means of sequential point by point burning by means of light beams, in particular laser beams, or also by etching.

The corrugation or roughness in accordance with the invention need only, within the scope of the invention, extend over the part surfaces of the grip region 72 which are contacted by the operating hand.

The above-described features of the superficial surface structure in the grip region are suitable also for handpieces which are straight.

The production of the grip sleeve from plastics makes it possible also to manufacture the sleeve coloured throughout, in several colours. By this means not only can particular wishes by the person carrying out the treatment—with regard to colour—be taken into consideration, but it is also possible to use the colours for indicating particular types of handpiece 1 or of instrument 2, for example particular drive types (speeds of rotation).

I claim:

1. Medical or dental handpiece having a grip sleeve which extends along a longitudinal axis and has at a forward end thereof, a tool holder with a mounting device for a treatment tool arranged along or transversely of the longitudinal axis of the handpiece, and is releasibly connectable at its rear end with a supply part by means of a coupling device, the grip sleeve having a grip region which includes an external surface that is graspable by an operating hand a superficial surface structure which improves the grippability, at least at corresponding part regions of said external surface, the superficial surface structure being formed by means of circumferentially running grooves and corrugations alternating with one another and having an axial spacing from one another, the grooves and corrugations being concavely and convexly rounded in axial section, the grooves and corrugations having a radius in the range of 3 to 5 millimeters, the spacing between adjacent grooves being in the range of 2 to 4 millimeters and the depth of the grooves being in the range of 0.05 to 0.3 millimeters.

2. Handpiece according to claim 1, characterized in that, the grip sleeve is of a material which can be formed in a mold, said material being chosen from the group consisting of metal, plastics and ceramics.

3. Handpiece according to claim 1, characterized in that, said coupling device is a rotary/plug-in coupling, and further characterized in that, rear and forward reinforcing sleeves are placed in a rear end region and a forward end region, respectively, of the grip sleeve, the rear reinforcing sleeve having associated coupling parts for the rotary/plug-in coupling, and the tool holder being insertable into the forward reinforcing sleeve with a plug-in coupling pin and fixable therein by means of a fixing device.

4. Handpiece according to claim 3, characterized in that, in a middle region thereof, an internal cylindrical hole into which a forward end region of the rear sleeve is placed and centered by means of bearing and rotary force transmission parts.

5. Handpiece according to claim 3, characterized in that, the rear sleeve is biased against or axially confined by a rearwardly facing shoulder surface arranged in the grip sleeve by means of a fixing element which is placed in and fixed in the grip sleeve.

6. Handpiece according to claim 3, characterized in that, there is associated with the handpiece at least one radial spacing sleeve, which is placed in the grip sleeve, with tolerance, in the region of the forward end on rear reinforcing, which spacing sleeve provides with its free internal cross-section a mounting hole for drive and/or bearing parts of a drive train.

7. Handpiece according to claim 3, characterized in that, the outer surface of a grip sleeve, has a roughness having a depth of roughening of about 1.5 to 3.5 μm.

8. Handpiece according to claim 7, characterized in that, the roughness is the product of at least one of molding and eroding.

9. Handpiece according to claim 3, characterized in that, the fixing device for the tool holder is formed by a pin-like fixing element which penetrates the grip sleeve, is fitted into a hole of the forward sleeve from the outside, and has a fixing portion which engages into a fixing recess.

10. Handpiece according to claim 1, characterized in that, each of said grooves and corrugations is shaped, in cross-section, with a radius, and in that the radius of the grooves and corrugations is approximately 4 mm.

11. Handpiece according to claim 1, characterized in that, the spacing between mutually neighboring corrugations is approximately 3.1 mm.

12. Handpiece according to claim 1, characterized in that, said grooves have a depth of approximately 0.15 mm.

* * * * *